United States Patent [19]

Watanabe et al.

[11] Patent Number: 5,268,488

[45] Date of Patent: Dec. 7, 1993

[54] ACRYLATE COMPOUND, PREPARATION PROCESS THEREOF AND FUNGICIDE USING THE SAME

[75] Inventors: Masanori Watanabe; Toshinobu Tanaka; Hisato Kobayashi; Shuji Yokoyama; Hideaki Umeyama, all of Ube, Japan

[73] Assignee: Ube Industries, Ltd., Yamaguchi, Japan

[21] Appl. No.: 943,470

[22] Filed: Sep. 11, 1992

[30] Foreign Application Priority Data

Sep. 13, 1991 [JP] Japan .................. 3-308594
Nov. 22, 1991 [JP] Japan .................. 3-354221

[51] Int. Cl.$^5$ .................. C07D 207/30; C07D 255/00
[52] U.S. Cl. .................. 548/561; 549/366; 558/391; 560/12; 560/13; 560/16
[58] Field of Search .............. 560/12, 13, 16; 558/391; 548/561; 549/366

[56] References Cited

U.S. PATENT DOCUMENTS 4,723,034 2/1988 Schirmer et al. .................. 560/60

FOREIGN PATENT DOCUMENTS 0178826 10/1985 European Pat. Off. .
0378308 1/1990 European Pat. Off. .

Primary Examiner—C. Warren Ivy
Assistant Examiner—Raymond Covington
Attorney, Agent, or Firm—Finnegan, Henderson, Farabow, Garrett & Dunner

[57] ABSTRACT

Disclosed are an acrylate series compound represented by the following formula:

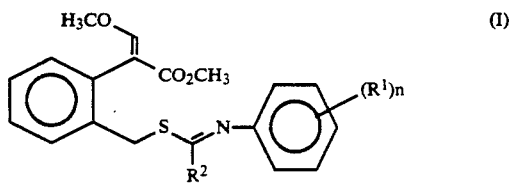

wherein $R^1$ represents a $C_{1-10}$ alkoxy group, a halogen atom, a $C_{1-6}$ alkyl group, a nitro group, a $C_{1-6}$ alkylamino group, a $C_{1-6}$ alkylthio group, a halo $C_{1-6}$ alkyl group, a pyrrole group, a $C_{1-6}$ alkylsulfonyl group, a cyano group, a $C_{1-6}$ mono- or dialkylaminosulfonyl group, a phenoxy group which may have a $C_{1-6}$ alkoxy group, a benzyloxy group, a halo $C_{1-6}$ alkoxy group, a $C_{3-6}$ alkenyloxy group, a hydroxyl group, a $C_{2-7}$ cyanoalkoxy group, a $C_{3-6}$ alkynyloxy group, a $C_{1-6}$ alkoxy group substituted by a $C_{3-6}$ cycloalkyl group, a $C_{1-6}$ alkoxy group substituted by a $C_{1-6}$ alkoxy group, a $C_{2-7}$ alkoxycarbonyl group or a $C_{2-7}$ acyl; $R^2$ represents a $C_{3-8}$ cycloalkyl group which may have a $C_{1-6}$ alkyl group; n represents an integer of 0 to 5; a plural number of $R^1$s may be the same or different; and when n is 2, two $R^1$s may be linked with each other and condensed to a benzene ring to form a saturated 4- to 8-membered ring or a dioxolan ring together with carbon atoms to which they are bonded, a preparation process thereof and a fungicide using the same as an active ingredient.

6 Claims, No Drawings

ACRYLATE COMPOUND, PREPARATION PROCESS THEREOF AND FUNGICIDE USING THE SAME

BACKGROUND OF THE INVENTION

This invention relates to a novel acrylate series compound useful as a fungicide and a preparation process thereof.

As an acrylate series compound having a fungicidal effect, there have been known those described in Japanese Provisional Patent Publications No. 106538/1986 (corresponding to European Patent Publication No. 0 178 826 A2) and No. 288806/1990 (corresponding to European Patent Publication No. 0 378 308 A1).

However, the compounds described in these publications have problems that they do not exhibit satisfactory fungicidal effects and cause chemical damage to agricultural crops.

SUMMARY OF THE INVENTION

An object of the present invention is to provide a novel acrylate series compound, a preparation process thereof and a fungicide using the same as an active ingredient.

The present inventors have studied intensively in order to solve the above task, and consequently found that a novel acrylate series compound has an extremely excellent fungicidal effect on agricultural crops and causes extremely small chemical damage thereto, to accomplish the present invention.

That is, the first invention relates to an acrylate series compound represented by the following formula:

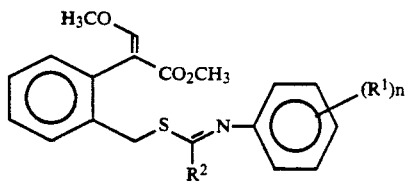

wherein $R^1$ represents an alkoxy group having 1 to 10 carbon atoms, a halogen atom, an alkyl group having 1 to 6 carbon atoms, a nitro group, an alkylamino group having 1 to 6 carbon atoms, an alkylthio group having 1 to 6 carbon atoms, a haloalkyl group having 1 to 6 carbon atoms, a pyrrole group, an alkylsulfonyl group having 1 to 6 carbon atoms, a cyano group, a mono- or dialkylaminosulfonyl group having 1 to 6 carbon atoms, a phenoxy group which may have an alkoxy group having 1 to 6 carbon atoms, a benzyloxy group, a haloalkoxy group having 1 to 6 carbon atoms, an alkenyloxy group having 3 to 6 carbon atoms, a hydroxyl group, a cyanoalkoxy group having 2 to 7 carbon atoms, an alkynyloxy group having 3 to 6 carbon atoms, an alkoxy group having 1 to 6 carbon atoms substituted by a cycloalkyl group having 3 to 6 carbon atoms, an alkoxy group having 1 to 6 carbon atoms substituted by an alkoxy group having 1 to 6 carbon atoms, an alkoxycarbonyl group having 2 to 7 carbon atoms or an acyl group having 2 to 7 carbon atoms; $R^2$ represents a cycloalkyl group having 3 to 8 carbon atoms which may have an alkyl group having 1 to 6 carbon atoms; n represents an integer of 0 to 5; a plural number of $R^1$s may be the same or different; and when n is 2, two $R^1$s may be linked with each other and condensed to a benzene ring to form a saturated 4- to 8-membered ring or a dioxolan ring together with carbon atoms to which they are bonded.

The second invention relates to a process for preparing the above compound (I), which comprises reacting a compound represented by the following formula:

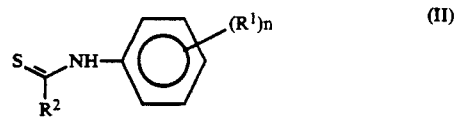

wherein $R^1$, $R^2$ and n each have the same meanings as defined above, with a compound represented by the following formula:

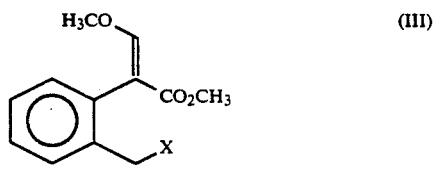

wherein X represents an eliminatable group, in the presence of a base.

The third invention relates to a fungicide comprising the above compound (I) as an active ingredient.

DESCRIPTION OF THE PREFERRED EMBODIMENTS

In the following, the present invention is explained in detail.

In the novel acrylate series compound (compound (I)) which is a desired compound described above, and starting materials (compound (II) and compound (III)) thereof, $R^1$, $R^2$, X and substitution positions of $(R^1)_n$ are as described below.

As $R^1$, there may be mentioned an alkoxy group having 1 to 10 carbon atoms, a halogen atom, an alkyl group having 1 to 6 carbon atoms, a nitro group, an alkylamino group having 1 to 6 carbon atoms, an alkylthio group having 1 to 6 carbon atoms, a haloalkyl group having 1 to 6 carbon atoms, a pyrrole group, an alkylsulfonyl group having 1 to 6 carbon atoms, a cyano group, a mono- or dialkylaminosulfonyl group having 1 to 6 carbon atoms, a phenoxy group which may have an alkoxy group having 1 to 6 carbon atoms, a benzyloxy group, a haloalkoxy group having 1 to 6 carbon atoms, an alkenyloxy group having 3 to 6 carbon atoms, a hydroxyl group, a cyanoalkoxy group having 2 to 7 carbon atoms, an alkynyloxy group having 3 to 6 carbon atoms, an alkoxy group having 1 to 6 carbon atoms substituted by a cycloalkyl group having 3 to 6 carbon atoms, an alkoxy group having 1 to 6 carbon atoms substituted by an alkoxy group having 1 to 6 carbon atoms, an alkoxycarbonyl group having 2 to 7 carbon atoms and an acyl group having 2 to 7 carbon atoms.

As the alkoxy group having 1 to 10 carbon atoms of $R^1$, there may be mentioned a straight or branched alkoxy group. Preferred are those having 1 to 8 carbon atoms, and more preferred are those having 1 to 6 carbon atoms (e.g. methoxy, ethoxy, propoxy, butoxy, pentyloxy and hexyloxy). The positions of these substituents are not particularly limited, but preferably 3-position, 4-position, 3- and 4-positions, 3- and 5-positions or 3-, 4- and 5-positions in a methoxy group, 4-position in an ethoxy group, a butoxy group, a pentyloxy group and a hexyloxy group, and preferably 3-position and/or 4-position in a propoxy group.

The position of the nitro group of $R^1$ is not particularly limited, but preferably at least one of 2-, 3- and 4-positions.

As the halogen atom of $R^1$, there may be mentioned a chlorine atom, an iodine atom, a bromine atom and a fluorine atom, and preferred are a chlorine atom and a fluorine atom. The positions of these substituents are not particularly limited, but preferably 3-position and/or 4-position.

As the alkyl group having 1 to 6 carbon atoms of $R^1$, there may be mentioned a straight or branched alkyl group, and preferred are those having 1 to 4 carbon atoms (e.g. methyl, ethyl, propyl and butyl). The positions of these substituents are not particularly limited, but preferably at least one of 2-, 3-, 4- and 5-positions in a methyl group, and preferably 3-position and/or 4-position in an ethyl group.

As the alkylamino group having 1 to 6 carbon atoms of $R^1$, there may be mentioned those having a straight or branched alkyl group, and preferred are those having an alkyl group having 1 to 4 carbon atoms (the same one as described above). The most preferred alkylamino group is dimethylamino, and the position of the substituent is not particularly limited, but preferably 4-position.

As the alkylthio group having 1 to 6 carbon atoms of $R^1$, there may be mentioned those having a straight or branched alkyl group. Preferred are those having an alkyl group having 1 to 4 carbon atoms (the same one as described above), and more preferred are those having a methyl group (methylthio). The positions of these substituents are not particularly limited, but preferably 3-position.

As the haloalkyl group having 1 to 6 carbon atoms of $R^1$, there may be mentioned those having a straight or branched alkyl group, and preferred are those having an alkyl group having 1 to 4 carbon atoms (the same one as described above). On the other hand, as the halogen atom, there may be mentioned a chlorine atom, an iodine atom, a bromine atom and a fluorine atom, and preferred is a fluorine atom. The most preferred haloalkyl group is a trifluoromethyl group, and the position of the substituent is not particularly limited, but preferably 3-position.

The position of the pyrrole group of $R^1$ is not particularly limited, but preferably 3-position.

As the alkylsulfonyl group having 1 to 6 carbon atoms of $R^1$, there may be mentioned those having a straight or branched alkyl group, and preferred are those having an alkyl group having 1 to 4 carbon atoms (the same one as described above). The most preferred alkylsulfonyl group is a methylsulfonyl group, and the position of the substituent is not particularly limited, but preferably 3-position.

The position of the cyano group of $R^1$ is not particularly limited, but preferably 3-position and/or 4-position.

As the mono- or dialkylaminosulfonyl group of $R^1$, there may be mentioned those having a straight or branched alkyl group having 1 to 6 carbon atoms, and preferred are those having an alkyl group having 1 to 4 carbon atoms (the same one as described above). The most preferred alkylaminosulfonyl group is a dimethylaminosulfonyl group, and the position of the substituent is not particularly limited, but preferably 3-position.

In the phenoxy group which may have an alkoxy group having 1 to 6 carbon atoms to of $R^1$, the alkoxy group may include those having a straight or branched alkoxy group, and the carbon number of the alkoxy group is preferably 1 to 4 (the same one as described above). The most preferred phenoxy group which may have an alkoxy group is a phenoxy group or a methoxyphenoxy group.

The position of the benzyloxy group of $R^1$ is not particularly limited, but preferably 3-position and/or 4-position.

As the haloalkoxy group having 1 to 6 carbon atoms of $R_1$, there may be mentioned those having a straight or branched alkoxy group, and preferred are those having an alkoxy group having 1 to 4 carbon atoms (the same one as described above). On the other hand, as the halogen atom, there may be mentioned a chlorine atom, an iodine atom, a bromine atom and a fluorine atom, and preferred is a fluorine atom. The most preferred haloalkoxy group is a trifluoromethoxy group, and the position of the substituent is not particularly limited, but preferably 4-position.

The alkenyloxy group having 3 to 6 carbon atoms of $R^1$ may be straight or branched, and preferred is an allyloxy group. The substitution position is not particularly limited, but preferably 3-position and/or 4-position.

The position of the hydroxyl group of $R^1$ is not particularly limited, but preferably 3-position and/or 4-position.

As the cyanoalkoxy group having 2 to 7 carbon atoms of $R^1$, there may be mentioned those having a straight or branched alkoxy group. Preferred are those having an alkoxy group having 1 to 4 carbon atoms (the same one as described above), and more preferred is a cyanomethoxy group. The position of the substituent is not particularly limited, but preferably 3-position and/or 4-position.

The alkynyloxy group having 3 to 6 carbon atoms of $R^1$ may be straight or branched, and preferred is a propargyloxy group. The position of the substituent is not particularly limited, but preferably 4-position.

In the alkoxy group having 1 to 6 carbon atoms substituted by a cycloalkyl group having 3 to 6 carbon atoms of $R^1$, the carbon number of the cycloalkyl group is preferably 3 to 4, and the carbon number of the alkoxy group is preferably 1 to 4 (the same one as described above), and more preferred is a methoxy group. The most preferred alkoxy group having a cycloalkyl group is a cyclopropylmethoxy group, and the position of the substituent is not particularly limited, but preferably 4-position.

In the alkoxy group having 1 to 6 carbon atoms substituted by an alkoxy group having 1 to 6 carbon atoms of $R^1$, both alkoxy groups may be straight or branched. Preferred is an alkoxy group having 1 to 4 carbon atoms (the same one as described above), and more preferred is a methoxyethoxy group. The position of the substituent is not particularly limited, but preferably 4-position.

As the alkoxycarbonyl group having 2 to 7 carbon atoms of $R^1$, there may be mentioned a carbonyl group substituted by a straight or branched alkoxy group having 1 to 6 carbon atoms, and the carbon number of the alkoxy group is preferably 1 to 4, more preferably 1 (methoxycarbonyl) or 2 (ethoxycarbonyl). The position of the substituent is not particularly limited, but preferably 4-position.

As the acyl group having 2 to 7 carbon atoms of $R^1$, there may be mentioned those having a straight or branched alkyl group having 1 to 6 carbon atoms, and the carbon number of the alkyl group is preferably 1 to 4, more preferably 1 (acetyl). The position of the substituent is not particularly limited, but preferably 4-position.

In the cycloalkyl group having 3 to 8 carbon atoms which may have an alkyl group having 1 to 6 carbon atoms of $R^2$, the carbon number of the cycloalkyl group is preferably 3 to 6, more preferably 3 to 4, and the carbon number of the alkyl group is preferably 1 to 4 (the same one as described above), and more preferred is a methyl group. The most preferred cycloalkyl group which may have an alkyl group is cyclopropyl, 1-methylcyclopropyl, 2-methylcyclopropyl and cyclobutyl.

The eliminatable group X is not particularly limited, and may include, for example, a halogen atom (e.g. chlorine, bromine or iodine), an alkanesulfonyloxy group which may be substituted by a halogen (e.g. methanesulfonyloxy, ethanesulfonyloxy and trifluoromethanesulfonyloxy), and an arylsulfonyloxy group (e.g. benzenesulfonyloxy and p-toluenesulfonyloxy).

n represents an integer of 0 to 5, preferably an integer of 0 to 3, and when n is 2, two $R^1$s may be linked with each other and condensed to a benzene ring to form a saturated 4- to 8-membered ring or a dioxolan ring together with carbon atoms to which they are bonded. The saturated 4- to 8-membered ring is preferably a 6-membered ring (e.g. a ring as shown in Compound 6 in Table 1), and as the dioxolan ring, there may be mentioned, for example, a ring as shown in Compound 62 in Table 1.

The compound (I) of the present invention can be synthesized generally by reacting the starting compounds (II) and (III) in a solvent in the presence of a base.

The solvent is not particularly limited so long as it does not participate in the present reaction directly, and may include, for example, chlorinated or unchlorinated aromatic, aliphatic or alicyclic hydrocarbons such as benzene, toluene, xylene, methylnaphthalene, petroleum ether, ligroin, hexane, chlorobenzene, dichlorobenzene, methylene chloride and cyclohexane; ethers such as diethyl ether, tetrahydrofuran and dioxane; ketones such as acetone and methyl ethyl ketone; amides such as N,N-dimethylformamide and N,N-dimethylacetamide; organic bases such as triethylamine, pyridine and N,N-dimethylaniline; 1,3-dimethyl-2-imidazolidinone; dimethyl sulfoxide; alcohols such as methanol and t-butanol; and a mixture of the above solvents.

The amount of the solvent to be used may be such an amount that the concentration of the compound (II) becomes in the range of 0.1 to 80% by weight, preferably such an amount that the concentration of the compound (II) becomes 0.1 to 40% by weight.

As the base, there may be mentioned, for example, potassium tert-butoxide, potassium hydride, sodium hydride, potassium hydroxide, sodium hydroxide, potassium carbonate and sodium carbonate, and preferred is potassium tert-butoxide.

The amount of the base to be used may be 1 to 3-fold moles based on the compound (II).

The reaction temperature is $-10°$ to $130°$ C., preferably $10°$ to $80°$ C.

The reaction time varies depending on the above concentration and temperature, but may be generally 0.5 to 8 hours.

The ratio of the starting compounds may be 0.1 to 4-fold moles, preferably 0.5 to 1.5-fold moles of the compound (III) based on the compound (II).

The compound (II) to be used in the present invention can be prepared easily by, for example, reacting an amide and phosphorus pentasulfide in a solvent such as benzene, toluene and xylene, if necessary by heating, according to the method described in "New Experiment Chemistry Lecture", vol. 14, III, p. 1829 (published by Maruzen). It can be also prepared easily by reacting an amide and a Lawesson's reagent ("Reagents for organic synthesis", 13, 38) by heating in a solvent.

As the compound (II), there may be mentioned, for example, the respective compounds (II) comprising the respective kinds of substituents corresponding to Compounds 1 to 69 shown in Table 1 (referred to as Compounds $(II)_1$ to $(II)_{69}$. Compound $(II)_1$ means a compound wherein n is 1, $R^1$ is $OCH_3$ at 3-position and $R^2$ is cyclopropyl in the formula represented by the compound (II)).

The compound (III) to be used in the present invention can be prepared easily by, for example, treating methyl-3-methoxy-2-(2'-methylphenyl)acrylate with a halogenating agent such as N-bromosuccinimide according to the method described in Japanese Provisional Patent Publication No. 280452/1986 (corresponding to U.S. Pat. No. 4,723,034).

After completion of the reaction, the desired compound (I) prepared as described above may be subjected to conventional post-treatments such as extraction, condensation and filtration, and purified suitably by a known means such as recrystallization and various chromatographies, if necessary.

As the compound (I), there may be mentioned, for example, Compounds 1 to 69 shown in Table 1 (Compound 1 means a compound wherein n is 1, $R^1$ is $OCH_3$ at 3-position and $R^2$ is cyclopropyl in the formula represented by the compound (I)).

The compound (I) of the present invention can be used for preventing and curing diseases of plants such as downey mildew (vegetables), late blight, downey mildew (grape), blast, brown rust (wheat), black spot and leaf spot, particularly exhibits remarkable fungicidal effects of preventing and curing downey mildew (cucumber), blast (rice), powdery mildew (barley) and brown rust (wheat).

The fungicide of the present invention contains at least one compound (I) as an active ingredient.

The compound (I) can be used singly, but may be preferably used by mixing with a carrier, a surfactant, a dispersant and an auxiliary (for example, prepared as a composition such as a dust, an emulsion, a fine granule, a granule, a wettable powder, an oily suspension and an aerosol) according to a conventional method.

As the carrier, there may be mentioned, for example, a solid carrier such as talc, bentonite, clay, kaolin, diatomaceous earth, white carbon, vermiculite, slaked lime, siliceous sand, ammonium sulfate and urea; a liquid carrier such as hydrocarbons (e.g. kerosine and mineral oil), aromatic hydrocarbons (e.g. benzene, toluene and xylene), chlorinated hydrocarbons (e.g. chloroform and carbon tetrachloride), ethers (e.g. dioxane and tetrahydrofuran), ketones (e.g. acetone, cyclohexanone and isophorone), esters (e.g. ethyl acetate, ethylene glycol acetate and dibutyl maleate), alcohols (e.g. methanol, n-hexanol and ethylene glycol), polar solvents (e.g. dimethylformamide and dimethylsulfoxide) and water; and a gas carrier such as air, nitrogen, carbon dioxide and freon (trade name, produced by Du Pont de Nemours & Co. Inc.) (in the case of a gas carrier, mixed spray can be carried out).

As the surfactant and dispersant which can be used for improving attachment of the present chemical to and absorption thereof in animals and plants, and improving characteristics such as dispersion, emulsification and spreading of the chemical, there may be mentioned, for example, alcohol sulfates, alkylsulfonate, lignosulfonate and polyoxyethylene glycol ether. Further, for improving properties of its formulation, for example, carboxymethyl cellulose, polyethylene glycol and gum arabic can be used as an auxiliary.

In preparation of the present chemical, the above carrier, surfactant, dispersant and auxiliary can be used singly or in a suitable combination, respectively, depending on the respective purposes.

When the compound (I) of the present invention is made into formulations, the concentration of the active ingredient is generally 1 to 50% by weight in an emulsion, generally 0.3 to 25% by weight in a dust, generally 1 to 90% by weight in a wettable powder, generally 0.5 to 5% by weight in a granule, generally 0.5 to 5% by weight in an oily suspension, and generally 0.1 to 5% by weight in an aerosol.

These formulations can be provided for various uses by diluting them to have a suitable concentration and spraying them to stems and leaves of plants, soil and paddy field surface, or by applying them directly thereto, depending on the purposes.

EXAMPLES

The present invention is described in detail by referring to Reference example and Examples, but the scope of the present invention is not limited by these examples.

REFERENCE EXAMPLE 1

Synthesis of compound (II) and compound (III)

(1) Synthesis of compound (II)

Synthesis of cyclopropane carbothio-m-methoxyanilide

In 30 ml of toluene was dissolved 5.7 g (30 mmole) of cyclopropane carbo-m-methoxy-anilide, and 3 g of phosphorus pentasulfide was added thereto. The mixture was stirred at 80° C. for 1 hour.

The supernatant was removed by filtration, and the residue was extracted with toluene three times. The residue and the supernatant were treated by a silica gel column, and the solvent was removed by evaporation under reduced pressure to obtain 3.9 g (yield: 62%) of the title compound as yellow crystals.

(2) Synthesis of compound (III)

Synthesis of (E)-2-(2'-bromomethylphenyl)-3-methoxyacrylate

In 60 ml of carbon tetrachloride were dissolved 8.83 g of methyl (E)-2-(2'-methylphenyl)-3-methoxyacrylate and 7.6 g of N-bromosuccinimide, and 0.3 g of benzoyl peroxide was added thereto. The mixture was refluxed by heating for 4 hours. The reaction mixture was cooled to room temperature, and filtered. The filtrate was condensed and crystallized from n-hexane to obtain 11.6 g (yield: 95%) of the title compound as colorless crystals.

EXAMPLE 1

Synthesis of compound (I)

(1) Synthesis of (E)-2-[2'-(cyclopropyl(3"-methoxyphenylimino)methylthiomethyl)phenyl]-3-methoxyacrylate (Compound 1)

In 15 ml of tetrahydrofuran were dissolved 0.48 g (25 mmole) of cyclopropanecarbothio-m-methoxyanilide and 0.71 g (25 mmole) of (E)-2-(2'-bromomethylphenyl)-3-methoxyacrylate, and 30 mmole of potassium tert-butoxide was added thereto. The mixture was stirred at 60° C. for 2 hours.

After completion of the reaction, the reaction mixture was cooled to room temperature, and water was added thereto. The mixture was extracted with ether, and the extract was washed with a saturated saline solution and dried. Subsequently, the solvent was removed by evaporation under reduced pressure.

The resulting residue was isolated by silica gel column chromatography (Wako Gel C-200 (trade name, manufactured by Wako Junyaku K.K.), eluted by toluene:ethyl acetate=(1:0) to (10:1)) to obtain 0.82 g (yield: 80%) of the title compound as a colorless oily product.

(2) Syntheses of other compounds shown in Table 1

In the same manner as in Example 1, the other compounds shown in Table 1 were synthesized by using the compound (II) and compound (III) corresponding to the starting materials of the desired compound (I).

TABLE 1

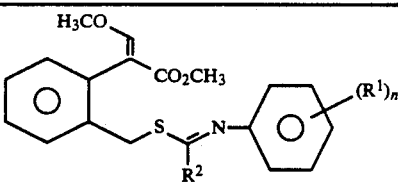

| Compound | $(R^1)_n$ | $R^2$ | Physical properties |
| --- | --- | --- | --- |
| 1 | —⟨OCH₃⟩ | ◁ | Data (1) |

TABLE 1-continued

[Structure: methyl (E)-2-methoxyimino-2-[2-(substituted-thioimidoylmethyl)phenyl]acetate with $(R^1)_n$ on N-phenyl and $R^2$ on imidoyl carbon]

| Compound | $(R^1)_n$-phenyl | $R^2$ | Physical properties |
|---|---|---|---|
| 2 | 4-Cl-phenyl | " | $n_D^{25.0}$ 1.5962 |
| 3 | 4-C$_2$H$_5$-phenyl | " | $n_D^{24.0}$ 1.5919 |
| 4 | 2-Cl-phenyl | " | $n_D^{23.0}$ 1.5927 |
| 5 | 2,4-(OCH$_3$)$_2$-phenyl | " | Data (5) |
| 6 | 5,6,7,8-tetrahydronaphthyl | " | $n_D^{27.0}$ 1.6025 |
| 7 | 2,3-(OCH$_3$)$_2$-phenyl | " | $n_D^{26.0}$ 1.5902 |
| 8 | 2-NO$_2$-3-CH$_3$-phenyl | " | $n_D^{25.0}$ 1.5996 |
| 9 | 2,3,4-(OCH$_3$)$_3$-phenyl | " | $n_D^{24.0}$ 1.5951 |
| 10 | 2-OCH$_3$-4-Cl-phenyl | " | $n_D^{24.0}$ 1.6002 |
| 11 | 4-F-phenyl | cyclopropyl | $n_D^{24.4}$ 1.5970 |
| 12 | phenyl | " | $n_D^{24.0}$ 1.5906 |

TABLE 1-continued
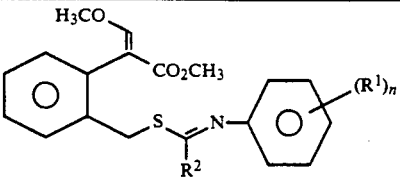
| Compound | (R¹)ₙ ⟨phenyl⟩ | R² | Physical properties |
|---|---|---|---|
| 13 | 4-OCH₃-phenyl | cyclobutyl | $n_D^{23.8}$ 1.5928 |
| 14 | 2,3-(H₃CO)-phenyl | cyclopropyl | $n_D^{23.4}$ 1.5938 |
| 15 | 4-N(CH₃)₂-phenyl | " | $n_D^{24.8}$ 1.6029 |
| 16 | 4-SCH₃-phenyl | " | $n_D^{25.5}$ 1.6015 |
| 17 | 4-CF₃-phenyl | " | $n_D^{24.0}$ 1.5667 |
| 18 | 4-OC₂H₅-phenyl | " | $n_D^{25.0}$ 1.5853 |
| 19 | 3-OC₂H₅-phenyl | " | $n_D^{25.0}$ 1.5957 |
| 20 | 2-F-phenyl | " | Data (20) |
| 21 | 2,3-(CH₃)₂-phenyl | cyclopropyl | $n_D^{26.0}$ 1.5996 |
| 22 | 2,6-(CH₃)₂-phenyl | " | $n_D^{25.0}$ 1.5986 |
| 23 | 3-NO₂-phenyl | " | m.p. 84~87° C. |

TABLE 1-continued

[Structure: H3CO, CO2CH3 methyl methoxyacrylate group on benzene ring with CH2-S-C(R2)=N-phenyl(R1)n]

| Compound | (R¹)ₙ-phenyl | R² | Physical properties |
|---|---|---|---|
| 24 | 4-NO₂-phenyl | " | m.p. 112~113° C. |
| 25 | 2-O₂N-phenyl | " | $n_D^{24.0}$ 1.6090 |
| 26 | 4-(pyrrolidin-1-yl)-phenyl | " | Data (26) |
| 27 | 4-OCH₃-phenyl | " | $n_D^{24.0}$ 1.5928 |
| 28 | 4-OCH₃-phenyl | cyclopropyl | $n_D^{24.0}$ 1.5989 |
| 29 | 4-OCH₃-phenyl | cyclopropyl (methyl-substituted) | $n_D^{25.0}$ 1.5897 |
| 30 | 4-SO₂CH₃-phenyl | cyclopropyl | Data (30) |
| 31 | 4-OCH(CH₃)₂-phenyl | cyclopropyl | $n_D^{20.0}$ 1.5815 |
| 32 | 3-NO₂-4-F-phenyl | " | $n_D^{21.0}$ 1.6024 |
| 33 | 3-CN-phenyl | " | $n_D^{17.0}$ 1.6053 |
| 34 | 4-CN-phenyl | " | m.p. 110~113° C. |

TABLE 1-continued
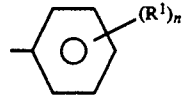
| Compound | (R¹)ₙ group | R² | Physical properties |
|---|---|---|---|
| 35 | —⌬—SO₂N(CH₃)₂ | " | $n_D^{21.0}$ 1.5887 |
| 36 | —⌬—O—⌬ (H₃CO) | " | $n_D^{17.0}$ 1.6087 |
| 37 | —⌬—OCH₂—⌬ | " | $n_D^{19.0}$ 1.6135 |
| 38 | —⌬—OCF₃ | " | $n_D^{20.0}$ 1.5585 |
| 39 | —⌬(Cl)(CH₃) | " | $n_D^{20.0}$ 1.6087 |
| 40 | —⌬(NO₂)(OCH₃) | " | m.p. 154.0~154.5° C. |
| 41 | —⌬(NO₂)—OCH₂CH=CH₂ | ▷ | $n_D^{18.0}$ 1.6098 |
| 42 | —⌬(Cl)(OH)(Cl) | " | $n_D^{25.0}$ 1.6074 |
| 43 | —⌬—OCH₂CH=CH₂ | " | $n_D^{27.0}$ 1.5814 |
| 44 | —⌬—OCH₂CH₂CH₃ | " | $n_D^{25.0}$ 1.5930 |

TABLE 1-continued

[Structure at top: a benzene ring bearing =C(OCH₃)CO₂CH₃ substituent and a CH₂-S-C(R²)=N-Ar(R¹)ₙ group]

| Compound | (R¹)ₙ on aryl | R² | Physical properties |
|---|---|---|---|
| 45 | 4-OH-phenyl | " | $n_D^{25.0}$ 1.5843 |
| 46 | 4-OCH₂CN-phenyl | " | $n_D^{25.0}$ 1.6108 |
| 47 | 4-OCH₂C≡CH-phenyl | " | $n_D^{26.0}$ 1.6022 |
| 48 | 4-OC₂H₅-phenyl | cyclobutyl | Data (48) |
| 49 | 4-OCH₂CH₂CH₃-phenyl | cyclopropyl | $n_D^{19.0}$ 1.5822 |
| 50 | 4-OCH₂CN-phenyl | " | Data (50) |
| 51 | 4-OCH₂C≡CH-phenyl | cyclopropyl | $n_D^{21.0}$ 1.5977 |
| 52 | 4-OCH₂-phenyl-phenyl | " | $n_D^{21.0}$ 1.6138 |
| 53 | 4-OH-phenyl | " | $n_D^{26.0}$ 1.5899 |
| 54 | 4-OCH₂CH=CH₂-phenyl | " | $n_D^{26.0}$ 1.5961 |
| 55 | 4-O(CH₂)₃CH₃-phenyl | " | $n_D^{25.0}$ 1.5720 |

TABLE 1-continued
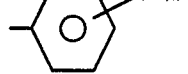
| Compound | (R¹)ₙ structure | R² | Physical properties |
|---|---|---|---|
| 56 |  —O(CH₂)₅CH₃ | " | $n_D^{24.0}$ 1.5736 |
| 57 | 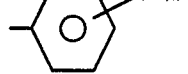 —O(CH₂)₇CH₃ | " | $n_D^{24.0}$ 1.5860 |
| 58 | 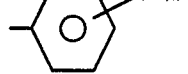 —O—CH₂CH₂CH(CH₃)₂ | " | $n_D^{24.0}$ 1.5821 |
| 59 | 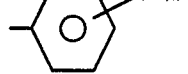 —OCH₃ | 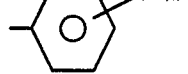 | $n_D^{24.0}$ 1.6076 |
| 60 |  —OCH₂—◁ | 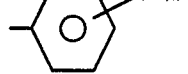 | $n_D^{22.0}$ 1.5830 |
| 61 |  —OH, —OCH₃ | 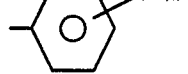 | $n_D^{21.0}$ 1.5870 |
| 62 |  | " | Data (62) |
| 63 | 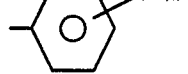 | " | $n_D^{24.0}$ 1.5816 |
| 64 | 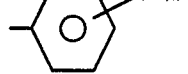 —OC₂H₄OCH₃ | " | $n_D^{18.0}$ 1.5851 |
| 65 | 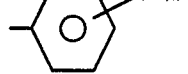 —COOCH₃ | " | $n_D^{22.0}$ 1.5975 |
| 66 | 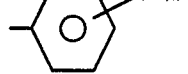 —COOC₂H₅ | " | Data (66) |

TABLE 1-continued

Structure (common to compounds):

H₃CO group with CO₂CH₃, attached to benzene ring with CH₂-S-C(R²)=N-phenyl-(R¹)ₙ

| Compound | —⟨phenyl⟩(R¹)ₙ | R² | Physical properties |
|---|---|---|---|
| 67 | —⟨C₆H₄⟩—COCH₃ | " | Data (67) |
| 68 | —⟨C₆H₄⟩—CH₃ | " | n_D^{24.0} 1.5855 |
| 69 | —⟨C₆H₄⟩—C₂H₅ | " | n_D^{24.0} 1.5848 |

Data (1): $^1$NMR (CDCl₃) δ ppm 0.74(2H, br, m), 0.98(2H, br, m), 1.80(1H, br, m), 3.68(3H, s), 3.78(3H, s), 3.82(3H, s), 4.15(2H, br, s), 6.45(2H, br), 6.60(1H, dd), 7.08~7.56(6H)

Data (5): $^1$NMR (CDCl₃) δ ppm 0.75(2H, br), 0.97(2H, br), 3.68(3H, s), 3.78(9H), 4.15(2H, s), 6.05(2H, br), 6.18(1H, s), 7.08~7.65(5H)

Data (20): $^1$NMR (CDCl₃) δ ppm 0.76(2H, br), 0.99(2H, br), 1.68(1H, br), 3.68(3H, s), 3.28(3H, s), 4.19(2H, s), 6.90~7.58(9H, m)

Data (26): $^1$NMR (CDCl₃) δ ppm 0.75(2H, br), 1.04(2H, br), 1.79(1H, br), 3.68(3H, s), 3.81(3H, s), 4.17(2H, s), 6.33~7.58(12H, m)

Data (30): $^1$NMR (CDCl₃) δ ppm 0.79(2H, br), 1.03(2H, br), 3.07(3H, s), 3.67(3H, s), 3.79(3H, s), 4.16(2H, s), 7.05~7.53(9H, m)

Data (48): $^1$NMR (CDCl₃) δ ppm 1.25(2H, m), 1.40(3H, t), 1.90(2H, m), 2.20(2H, m), 3.42(1H, m), 3.66(3H, s), 3.78(3H, s), 4.00(2H, t), 4.17(2H, brs), 6.78(2H, s), 7.03~7.16(1H, m), 7.15~7.35(4H, m), 7.38~7.50(1H, m), 7.56(1H, s)

Data (50): $^1$NMR (CDCl₃) δ ppm 0.7~1.02(4H, m), 1.65(1H, m), 3.68(3H, s), 3.78(3H, s), 4.16(2H, brs), 4.76(2H, brs), 6.80~7.52(8H, aromatic), 7.55(1H, s)

Data (62): $^1$NMR (CDCl₃) δ ppm 0.68~1.05(4H, m), 1.65~1.95(1H, m), 3.66(3H, s), 3.79(2H, s), 4.08~4.18(2H, br), 5.91(2H, S), 6.28~6.40(1H, m), 6.71~6.83(2H, m), 7.04~7.16(1H, m), 7.20~7.32(2H, m), 7.42~7.50(1H, m), 7.55(1H, s)

Data (66): $^1$NMR (CDCl₃) δ ppm 0.75(2H, m), 1.01(2H, m), 1.38(3H, t), 1.65(1H, m), 3.69(3H, s), 3.78(3H, s), 4.16(2H, brs), 4.35(2H, q), 6.89(2H, d), 7.08~7.49(4H, m), 7.56(1H, s), 8.00(2H, d)

Data (67): $^1$NMR (CDCl₃) δ ppm 0.76(2H, m), 1.01(2H, m), 1.68(1H, m), 2.57(3H, s), 3.68(3H, s), 3.78(3H, s), 4.16(2H, brs), 6.89(2H, d), 7.02~7.51(4H, m), 7.56(1H, s), 5.92(2H, d)

EXAMPLE 2

Preparation of formulations (1) Preparation of granule 5 parts by weight of Compound 1 was uniformly mixed with 35 parts by weight of bentonite, 57 parts by weight of talc, 1 part by weight of Neopelex powder (trade name, produced by Kao K.K.) and 2 parts by weight of sodium lignosulfonate, and then the mixture was kneaded with addition of a small amount of water, followed by granulation and drying, to obtain a granule.

(2) Preparation of wettable powder 10 parts by weight of Compound 1 was uniformly mixed with 69.75 parts by weight of kaolin, 18 parts by weight of white carbon, 1.8 parts by weight of Neopelex powder (trade name, produced by Kao K.K.) and 0.45 part by weight of Demol (trade name, produced by Kao K.K.), and then the mixture was pulverized to obtain a wettable powder.

(3) Preparation of emulsion 50 parts by weight of Compound 2 was uniformly mixed with 30 parts by weight of xylene by adding 10 parts by weight of Agrisol P-300 (trade name, produced by Kao K.K.), 5 parts by weight of Emulgen A-90 (trade name, produced by Kao K.K.) and Rheodol 460 (trade name, produced by Kao K.K.), and dissolved therein to obtain an emulsion.

(4) Preparation of dust

5 Parts by weight of Compound 2 was uniformly mixed with 50 parts by weight of talc and 45 parts by weight of kaolin to obtain a dust.

EXAMPLE 3

Tests of effects (1) Test of controlling effect on downey mildew (cucumber)

In plastic flowerpots having a diameter of 6 cm, one cucumber (variety: Sagami Hanshiro) was grown per one flowerpot, and to the young plants at 1.5 leaf stage, the wettable powders prepared from the desired compounds (I) shown in Table 1 as in Example 2 were diluted to 40 ppm with water containing a surfactant (0.01%), and sprayed in an amount of 20 ml per one flowerpot, respectively.

After spraying, the cucumbers were grown in a glass greenhouse for 2 days, and then zoosporangia of Pseudoperonospora cubensis prepared from infected leaves were sprayed uniformly to the back surfaces of the plant leaves to be inoculated thereinto.

After inoculation, the cucumbers were maintained in a dark place at 20° C. for 2 days, and then grown in a glass greenhouse for 5 days. The degree of lesion of downey mildew (cucumber) appeared on the first leaves was examined.

The effect of each chemical was evaluated by using 6 ranks as compared with the degree of lesion in the non-treated district (0: all area is infected, 1: lesion area is about 60%, 2: lesion area is about 40%, 3: lesion area is about 20%, 4: lesion area is 10% or less and 5: no lesion is observed). The results are shown in Table 2.

TABLE 2

| Test of controlling effect on downey mildew (cucumber) | |
|---|---|
| Compound | Effect |
| 1 | 5 |
| 2 | 5 |
| 4 | 5 |
| 5 | 5 |
| 7 | 5 |
| 8 | 5 |
| 13 | 5 |
| 16 | 5 |
| 17 | 5 |
| 18 | 5 |
| 19 | 5 |
| 20 | 5 |
| 27 | 5 |
| 30 | 5 |
| 32 | 5 |
| 33 | 5 |
| 34 | 5 |
| 36 | 4 |
| 37 | 5 |
| 39 | 5 |
| 40 | 5 |
| 41 | 5 |
| 43 | 5 |
| 44 | 5 |
| 45 | 5 |
| 46 | 4 |
| 47 | 5 |
| 48 | 4 |
| 49 | 5 |
| 50 | 5 |
| 51 | 5 |
| 54 | 5 |
| 55 | 5 |
| 60 | 5 |
| 63 | 5 |
| 68 | 4 |
| 69 | 4 |
| A | 0 |
| B | 2 |

As a control compound, Compound (A) (compound described in Japanese Provisional Patent Publication No. 106538/1986) or Compound (B) (compound described in Japanese Provisional Patent Publication No. 288806/1990) shown below was used.

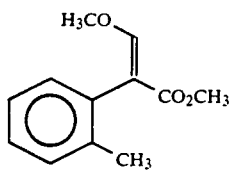

(A)

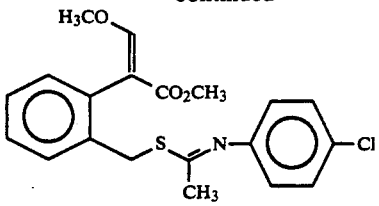

(B)

(2) Test of controlling effect on blast (rice)

In plastic flowerpots having a diameter of 6 cm, 10 rices (variety: Nipponbare) were grown per one flowerpot, and to the young plants at 1.5 leaf stage, the wettable powders prepared from the desired compounds (I) shown in Table 1 as in Example 2 were diluted to 40 ppm with water containing a surfactant (0.01%), and sprayed in an amount of 20 ml per one flowerpot, respectively.

After spraying, the rices were grown in a glass greenhouse for 2 days, and then a suspension of conidiospores of Pyricularia oryzae ($7 \times 10^4$ spore/ml) was sprayed uniformly to the plant leaves to be inoculated thereinto.

After inoculation, the rices were grown in a glass greenhouse at 28° C. for 5 days, and the degree of lesion of blast (rice) appeared on the leaves was examined.

The judgement results of the chemical effects are shown in Table 3 in the same manner as in the above (1).

TABLE 3

| Test of controlling effect on blast (rice) | |
|---|---|
| Compound | Effect |
| 1 | 4 |
| 19 | 4 |
| 27 | 4 |
| 30 | 4 |
| 32 | 5 |
| 33 | 4 |
| 43 | 4 |
| 47 | 4 |
| 52 | 4 |
| 54 | 4 |
| 60 | 4 |
| 62 | 5 |
| 65 | 4 |
| 68 | 4 |
| 69 | 4 |
| A | 0 |

(3) Test of controlling effect on powdery mildew (barley)

In plastic flowerpots having a diameter of 6 cm, 10 barleys (variety: Kuromugi) were grown per one flowerpot, and to the young plants at 1.5 leaf stage, the wettable powders prepared from the desired compounds (I) shown in Table 1 as in Example 2 were diluted to 200 ppm with water containing a surfactant (0.01%), and sprayed in an amount of 20 ml per one flowerpot, respectively.

After spraying, the barleys were grown in a glass greenhouse for 2 days, and then a suspension of conidiospores of Erysiphe graminis ($7 \times 10^4$ spore/ml) collected from infected leaves were sprayed uniformly over the plants to be inoculated thereinto.

After inoculation, the barleys were grown in a glass greenhouse for one week, and the degree of lesion of powdery mildew (barley) appeared on the first leaves was examined.

The judgement results of the chemical effects are shown in Table 4 in the same manner as in the above (1).

TABLE 4

Test of controlling effect on powdery mildew (barley)

| Compound | Effect |
|---|---|
| 1 | 5 |
| 2 | 4 |
| 5 | 4 |
| 9 | 4 |
| 11 | 4 |
| 12 | 4 |
| 16 | 4 |
| 17 | 5 |
| 18 | 4 |
| 19 | 4 |
| 27 | 5 |
| 29 | 5 |
| 31 | 5 |
| 32 | 4 |
| 33 | 5 |
| 36 | 4 |
| 37 | 4 |
| 38 | 5 |
| 39 | 4 |
| 41 | 4 |
| 52 | 4 |
| 53 | 4 |
| 62 | 4 |
| 63 | 4 |
| 65 | 4 |
| 68 | 4 |
| A | 0 |
| B | 2 |

(4) Test of controlling effect on brown rust (wheat)

In plastic flowerpots having a diameter of 6 cm, 10 wheats (variety: Kobushikomugi) were grown per one flowerpot, and to the young plants at 1.5 leaf stage, the wettable powders prepared from the desired compounds (I) shown in Table 1 as in Example 2 to 200 ppm with water containing a surfactant (0.01%), and sprayed in an amount of 20 ml per one flowerpot, respectively.

After spraying, the wheats were grown in a glass greenhouse for 2 days, and then a suspension of spores of *Puccinia dispersa* ($7 \times 10^4$ spore/ml) was sprayed uniformly to the plants to be inoculated thereinto.

After inoculation, the wheats were grown in a glass greenhouse for one weak, and the degree of lesion of brown rust (wheat) appeared on the first leaves was examined.

The judgement results of the chemical effects are shown in Table 5 in the same manner as in the above (1).

TABLE 5

Test of controlling effect on brown rust (wheat)

| Compound | Effect |
|---|---|
| 1 | 5 |
| 2 | 5 |
| 5 | 5 |
| 7 | 5 |
| 8 | 5 |
| 9 | 5 |
| 11 | 5 |
| 12 | 5 |
| 13 | 4 |
| 14 | 4 |
| 15 | 5 |
| 16 | 5 |
| 17 | 5 |
| 18 | 5 |
| 19 | 5 |
| 20 | 4 |
| 21 | 5 |
| 24 | 4 |
| 26 | 4 |
| 27 | 5 |
| 28 | 5 |
| 29 | 5 |
| 30 | 4 |
| 32 | 4 |
| 33 | 5 |
| 34 | 4 |
| 35 | 5 |
| 36 | 5 |
| 37 | 4 |
| 38 | 5 |
| 39 | 4 |
| 41 | 5 |
| 42 | 5 |
| 43 | 5 |
| 44 | 5 |
| 46 | 4 |
| 47 | 5 |
| 48 | 4 |
| 49 | 4 |
| 50 | 5 |
| 51 | 5 |
| 52 | 4 |
| 53 | 4 |
| 54 | 5 |
| 55 | 5 |
| 56 | 4 |
| 57 | 5 |
| 59 | 4 |
| 60 | 5 |
| 62 | 5 |
| 63 | 4 |
| 64 | 5 |
| 65 | 4 |
| 66 | 4 |
| 67 | 4 |
| 68 | 5 |
| 69 | 5 |
| A | 0 |

(5) Test of chemical damage to cucumber

In plastic flowerpots having a diameter of 6 cm, one cucumber (variety: Sagami Hanshiro) was grown per one flowerpot, and to the young plants at 1.5 leaf stage, the wettable powders prepared from the desired compounds (I) shown in Table 1 as in Example 2 were diluted to 500 ppm with water containing a surfactant (0.01%), and sprayed in an amount of 20 ml per one flowerpot, respectively.

After spraying, the cucumbers were grown in a glass greenhouse for 5 days, and then the degree of chemical damage was evaluated.

The chemical damage was evaluated by using 4 ranks (++: degree of chemical damage is severe, +: degree of chemical damage is light, ±: degree of chemical damage is extremely light, and −: no chemical damage is observed). The results are shown in Table 6.

As a control compound, Compound (B)(compound described in Japanese Provisional Patent Publication No. 288806/1990) shown in the above (1) was used.

(6) Test of chemical damage to rice

In plastic flowerpots having a diameter of 6 cm, ten rices (variety: Nipponbare) were grown per one flowerpot, and to the young plants at 1.5 leaf stage, the wettable powders prepared from the desired compounds (I) shown in Table 1 as in Example 2 were diluted to 500 ppm with water containing a surfactant (0.01%), and sprayed in an amount of 20 ml per one flowerpot, respectively.

After spraying, the rices were grown in a glass greenhouse for 5 days, and then the degree of chemical damage was evaluated.

The evaluation results of chemical damage are shown in Table 6 in the same manner as in the above (5).

(7) Test of chemical damage to barley

In plastic flowerpots having a diameter of 6 cm, ten barleys (variety: Kuromugi) were grown per one flowerpot, and to the young plants at 1.5 leaf stage, the wettable powders prepared from the desired compounds (I) shown in Table 1 as in Example 2 were diluted to 500 ppm with water containing a surfactant (0.01%), and sprayed in an amount of 20 ml per one flowerpot, respectively.

After spraying, the barleys were grown in a glass greenhouse for 5 days, and then the degree of chemical damage was evaluated.

The evaluation results of chemical damage are shown in Table 6 in the same manner as in the above (5).

(8) Test of chemical damage to wheat

In plastic flowerpots having a diameter of 6 cm, ten wheats (variety: Kobushikomugi) were grown per one flowerpot, and to the young plants at 1.5 leaf stage, the wettable powders prepared from the desired compounds (I) shown in Table 1 as in Example 2 were diluted to 500 ppm with water containing a surfactant (0.01%), and sprayed in an amount of 20 ml per one flowerpot, respectively.

After spraying, the wheats were grown in a glass greenhouse for 5 days, and then the degree of chemical damage was evaluated.

The evaluation results of chemical damage are shown in Table 6 in the same manner as in the above (5).

TABLE 6

| Compound | Test of chemical damage to crops | | | |
| --- | --- | --- | --- | --- |
| | Degree of chemical damage | | | |
| | Cucumber | Rice | Barley | Wheat |
| 1 | − | − | − | − |
| 2 | ± | − | − | − |
| 4 | ± | − | − | − |
| 13 | − | − | − | − |
| 14 | − | − | − | − |
| 15 | − | − | − | − |
| 16 | − | − | − | − |
| 18 | − | − | − | − |
| 19 | − | − | − | − |
| 20 | − | − | − | − |
| 21 | − | − | − | − |
| 23 | − | − | − | − |
| 24 | − | − | − | − |
| 25 | ± | − | − | − |
| 26 | − | − | − | − |
| 27 | ± | − | − | − |
| 28 | ± | − | − | − |
| 29 | ± | − | − | − |
| 30 | − | − | − | − |
| 31 | − | − | − | − |
| 34 | − | − | − | − |
| 35 | − | − | − | − |
| 36 | − | − | − | − |
| 37 | − | − | − | − |
| 40 | − | − | − | − |
| 42 | − | − | − | − |
| 43 | − | − | − | − |
| 44 | ± | − | − | − |
| 45 | − | − | − | − |
| 46 | ± | − | − | − |
| 48 | − | − | − | − |
| 49 | ± | − | − | − |
| 51 | ± | − | − | − |
| 52 | ± | − | − | − |
| 53 | − | − | − | − |
| 54 | − | − | ± | ± |
| 56 | ± | − | − | − |
| 57 | ± | − | − | − |
| 58 | ± | − | − | − |
| 59 | ± | − | − | − |
| 60 | − | − | − | − |
| 61 | − | − | − | − |
| 62 | ± | − | ± | − |
| 63 | ± | − | − | − |
| 64 | − | − | − | − |
| 65 | − | − | − | − |
| 66 | − | − | − | − |
| 67 | − | − | − | − |
| 68 | − | − | − | − |
| 69 | − | − | − | − |
| B | ++ | ++ | ++ | + |

As described above, the novel acrylate series compound of the present invention is an agricultural chemical useful as a fungicide.

We claim:

1. An acrylate compound represented by the following formula:

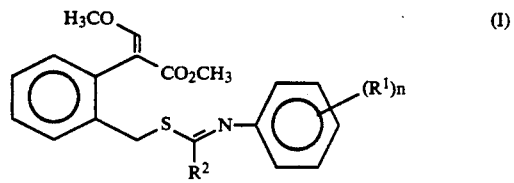

wherein $R^1$ represents an alkoxy group having 1 to 10 carbon atoms, a halogen atom, an alkyl group having 1 to 6 carbon atoms, a nitro group, an alkylamino group having 1 to 6 carbon atoms, an alkylthio group having 1 to 6 carbon atoms, a haloalkyl group having 1 to 6 carbon atoms, a pyrrole group, an alkylsulfonyl group having 1 to 6 carbon atoms, a cyano group, a mono- or dialkylaminosulfonyl group having 1 to 6 carbon atoms, a phenoxy group which may have an alkoxy group having 1 to 6 carbon atoms, a benzyloxy group, a haloalkoxy group having 1 to 6 carbon atoms, an alkenyloxy group having 3 to 6 carbon atoms, a hydroxyl group, a cyanoalkoxy group having 2 to 7 carbon atoms, an alkynyloxy group having 3 to 6 carbon atoms, an alkoxy group having 1 to 6 carbon atoms substituted by a cycloalkyl group having 3 to 6 carbon atoms, an alkoxy group having 1 to 6 carbon atoms substituted by an alkoxy group having 1 to 6 carbon atoms, an alkoxycarbonyl group having 2 to 7 carbon atoms or an acyl group having 2 to 7 carbon atoms; $R^2$ represents a cycloalkyl group having 3 to 8 carbon atoms which may have an alkyl group having 1 to 6 carbon atoms; n represents an integer of 0 to 5; a plural number of $R^1$s may be the same or different; and when n is 2, two $R^1$s may be linked with each other and condensed to a benzene ring to form a saturated 4- to 8-membered ring or a dioxolan ring together with carbon atoms to which they are bonded.

2. The compound according to claim 1, wherein $R^1$ is at least one selected from the group consisting of a $C_{1-6}$ alkoxy group, a nitro group, a chlorine atom, a fluorine atom, a $C_{1-4}$ alkyl group, a $C_{1-4}$ alkylamino group, a $C_{1-4}$ alkylthio group, a halo $C_{1-4}$ alkyl group, a pyrrole group, a $C_{1-4}$ alkylsulfonyl group, a cyano group, a $C_{1-4}$ alkylaminosulfonyl group, a phenoxy group which may be substituted by a $C_{1-4}$ alkoxy group, a benzyloxy group, a halo $C_{1-4}$ alkoxy group, a $C_{3-5}$ alkenyloxy group, a hydroxyl group, a cyano $C_{1-4}$ alkoxy group, a $C_{3-6}$ alkynyloxy group, a $C_{1-4}$ alkoxy group substituted by a $C_{3-4}$ cycloalkyl group, a $C_{1-4}$ alkoxy group substituted by a $C_{1-4}$ alkoxy group, a $C_{2-6}$ alkoxycarbonyl group and a $C_{2-5}$ acyl group.

3. The compound according to claim 1, wherein $R^1$ is at least one selected from the group consisting of a methoxy group, an ethoxy group, a propoxy group, a butoxy group, a pentyloxy group, a hexyloxy group, an isopentyloxy group, a nitro group, a chlorine atom, a fluorine atom, a methyl group, an ethyl group, a dimethylamino group, a methylthio group, a trifluoromethyl group, a pyrrole group, a methylsulfonyl group, a cyano group, a dimethylaminosulfonyl group, a phenoxy group, a methoxyphenoxy group, a benzyloxy group, a trifluoromethoxy group, an allyloxy group, a hydroxyl group, a cyanomethoxy group, a propargyloxy group, a cyclopropylmethoxy group, a methoxyethoxy group, a methoxycarbonyl group, an ethoxycarbonyl group and an acetyl group.

4. The compound according to claim 1, wherein $R^2$ is a cyclopropyl, 1-methylcyclopropyl, 2-methylcyclopropyl or cyclobutyl group.

5. The compound according to claim 1, wherein said compound is methyl (E)-2-[2'-{cyclopropyl(3''-methoxyphenylimino)methylthiomethyl}phenyl]-3-methoxyacrylate, methyl (E)-2-[2'-{cyclopropyl(3'',5''-dimethoxyphenylimino)methylthiomethyl}phenyl]-3-methoxyacrylate, methyl (E)-2-[2'-{cyclopropyl(4''-ethoxyphenylimino)methylthiomethyl}-phenyl]-3-methoxyacrylate, methyl (E)-2-[2'-{cyclopropyl(4''-methoxyphenylimino)methylthiomethyl}phenyl]-3-methoxyacrylate, methyl (E)-2-[2'-{(3''-cyanophenylimino)cyclopropylmethylthiomethyl}phenyl]-3-methoxyacrylate, methyl (E)-2-[2'-{cyclopropyl(4''-ethoxycarbonylphenylimino)-methylthiomethyl}phenyl]-3-methoxyacrylate or methyl (E)-2-[2'-{cyclopropyl(4''-ethylphenylimino)methylthiomethyl}phenyl]-3-methoxyacrylate.

6. A fungicide comprising the acrylate compound represented by the formula (I) according to claim 1 as an active ingredient and a fungicidally effective carrier.

* * * * *